United States Patent [19]
Abys et al.

[11] Patent Number: 5,275,711
[45] Date of Patent: Jan. 4, 1994

[54] ROTATING CYLINDER-THROWING POWER ELECTRODE

[75] Inventors: Joseph A. Abys, Warren; Igor V. Kadija, Ridgewood; Joseph J. Maisano, Jr., Denville, all of N.J.

[73] Assignee: AT&T Bell Laboratories, Murray Hill, N.J.

[21] Appl. No.: 901,049

[22] Filed: Jun. 19, 1992

[51] Int. Cl.$^5$ ............................................. G01N 27/26
[52] U.S. Cl. .................................. 204/434; 204/153.1; 204/400; 204/DIG. 7
[58] Field of Search ...................... 204/400, 434, DIG.

[56] References Cited

U.S. PATENT DOCUMENTS

| | | | |
|---|---|---|---|
| 3,215,609 | 11/1965 | Chapdelaine | 204/434 |
| 4,487,681 | 12/1984 | Cordes | 204/434 |
| 4,605,626 | 8/1986 | Beck | 204/212 |

OTHER PUBLICATIONS

H. E. Haring et al. "Current Distribution and Throwing Power in Electrodeposition", *Trans. Am. Electrochem. Soc.*, vol. 44, May 3, 1923, pp. 313–345.

T. C. Tan, "A Novel Experimental Cell for the Determination of the Throwing Power of an Electroplating System" *Jrnl. of Electrochemical Society*, vol. 134, No. 12, Dec. 1987, pp. 3011–3015.

T. C. Tan, "Model for Calculating Metal Distribution and Throwing Power of Plating Baths", *Plating and Surface Finishing* Jul. 1987, pp. 67–71.

ASTM 02.05 Designation: B 507-86-Standard Practice for Design of Articles to be Electroplated on Racks, Sep. 1986.

*Primary Examiner*—T. Tung
*Attorney, Agent, or Firm*—Oleg E. Alber

[57] ABSTRACT

This invention pertains to an apparatus and method for measuring throwing power of electroplating solutions. The apparatus is easy to use and gives reproducible measurements. The apparatus emulates the performance of a conventional Haring Blum cell. The major disadvantage of the standard Haring Blum cell is its limited aility to vary the solution mass transport, thus limiting its applicability to very low current density applications. Furthermore, even under low-mass transport conditions, non-uniform solution distribution is experienced leading to erroneous interpretation. This invention permits the study of throwing power of electroplating solutions under a whole variety of solution agitation. The invention embodies an instrument for and a method of measuring the throwing power of electrolytes. The instrument is in a form of an elongated cylindrical body adapted for rotation about its longitudinal axis and includes a fixed conductive anode element and at least two cathode elements, at least one of which is variably spaced from the anode element. Preferably, one cathode element is fixed relative to the anode element a first predetermined distance and another cathode element is spaced from the anode element a second variable distance which is a multiple of the first distance. The instrument also includes means for providing current to the anode element and equi-potentially to each of the cathode elements. The measuring includes providing each of the cathode elements with a pre-weighed removable metal foil, rotating the instrument which the anode and cathode elements are completely submerged in an electrolyte, applying current to the anode and the cathode elements, removing the metal foils from the cathode elements and weighing the metal foils with the deposit thereon to compare the weight of deposited metal at different cathode element positions.

5 Claims, 10 Drawing Sheets

ROTATING CYLINDER-THROWING POWER ELECTRODE

FIELD OF THE INVENTION

This invention pertains to an apparatus for and a method of measuring a throwing power of electroplating solutions.

BACKGROUND OF THE INVENTION

Throwing power is one of performance parameters of plating solutions that has held electroplaters' attention for many years. Among the many characteristics of electrodeposits, the most commonly specified by end users are macroscopic thickness uniformity and minimum and/or maximum thickness. The capability of a plating bath to give uniform thickness distribution is referred to as having a good throwing power. Deposition of a metal over an entire area of a complex part and leveling of the rough finishes are particularly important. Connectors with grooves, springs, tubing, stamped metal connectors and other complex stamped parts need uniform coverage of metals to meet specified functional requirements. Plate finish standards and end-users' specifications typically give minimum and maximum thickness criteria. Knowing, a priori, whether or not such requirements can be met, is quite challenging because the throwing power, as a parameter specific to each particular plating solution, is not readily available. Therefore, the plating engineer must develop the finishing processes which reproducibly provide acceptable quality. To accomplish this, one must rely on published information about the throwing power of commercially available plating baths. However, little reliable information is available which quantifies the throwing power. This is particularly true for modern electroplating solutions where high current densities usually require high solution agitation.

Since the 1920s an apparatus known as the Haring-Blum (HB) cell has been a standard tool for measuring throwing power. A schematic representation of a Haring-Blum cell, 80, is shown in FIG. 8. It is a rectangular container, 81, with positions for one anode element, 82, and two equi-potential cathode elements, 83 and 84, placed on either side of the anode. Current to the anode element and the cathode elements is provided from a current source 85 via conductors 86 and 87, respectively. By moving the anode element toward one or the other cathode element, various ratios of distances between the anode and the two cathodes may be preselected. The measurement is performed by weighing the deposit on each of the two cathode elements after simultaneous deposition on both. In the case of an "ideal" weight distribution, i.e., both deposits have equal weight. However, the reproducibility and the measurements performed with the Haring-Blum (HB) cell are rather limited. This is primarily due to the lack of well-defined and reproducible hydrodynamics, inability to provide high-speed solution agitation, and inability to attain high current densities.

Many modern electroplating cells employ fluid velocities of several meters per second, while the HB cell or similar equipment has a practical limit at 20–30 cm/s. Solution agitation is typically conducted by means of air bubbling or by magnetic stirrers, e.g. stirrer 88. Therefore, the information obtained under low to moderate agitation is not directly applicable to high-speed processes. The information obtained with the HB cell is limited to low current densities due to the inherent limitations of low solution agitation. Current densities of the order of up to 40 ASF and low solution agitation are amenable for application of the HB cell.

Solution agitation can affect the current distribution through secondary and tertiary current distribution effects and thus influence the throwing power. The electric field and its resulting primary current density distribution are the first order parameters which govern metal deposit distribution, Typically, the current density decreases as the distance from the anode increases. In order to overcome this primary current density distribution effect, commercial plating apparatus are designed to apply the kinetic and/or the transport of matter "adjustments" to the current density.

The kinetics adjustments can be divided into two kinds: the enhanced polarization at retained high current efficiency and enhanced polarization at reduced current efficiency. This results in the so-called secondary current density distribution, definable as a current density distribution which encompasses an additional "resistance" at the interface (polarization), which is not a function of part geometry and/or interelectrode gap. Thus, the strict dependence of current density on the part geometry and solution resistance can be reduced. An additional benefit is obtained when the polarization brings about a non-plating process (e.g. hydrogen evolution) so that the "excess" current is "consumed" without metal deposition.

The transport of matter is the key parameter which can influence throwing power. Generally, the polarization of metal deposition process (assuming the same metal in various chemical environments) is a result of two effects; one is the coordination shell composition and the other is the presence of additives. The coordination shell plays a role in the steps preceding discharge and immediately following the deposition, creating a thin solution layer which is chemically different than the bulk solution. Additives, byproducts and contaminants may also participate in the mechanism of deposition. The magnitude of these effects on metal distribution are a function of the transport of matter.

The transport of matter adjustment is performed with low concentration of depositing metal. Under these conditions, if solution agitation is relatively uniform across the plated part, one obtains the transport limited current at low current density. This results in the so-called tertiary current density distribution and leads to little or no change in the transport limited current density across the plated part, regardless of the magnitude of the excess current.

T. C. Tan undertook to give an electrochemical interpretation to the throwing power, in which electroplating parameters such as electrode polarization and overall voltage are taken into consideration. See T. C. Tan, "Model for Calculating Metal Distribution And Throwing Power of Plating Baths", *Plating and Surface Finishing*, July 1987, pages 67–71. See also Thiam Chye Tan, "A Novel Experimental Cell for the Determination of the Throwing Power of an Electroplating System", *Journal of Electrochemical Society: Electrochemical Science and Technology*, Vol. 134, No. 12, December 1987, pages 3011 et seq. Tan has devised his own cell design for throwing power measurements. This multicompartment cell contains anodes and cathodes covering a range of distances, while mixing is provided by gas spargers. Although the uniformity of agitation has been improved over the Haring Blum cell, it is still limited by low solution agitation rates and restricted solution volume.

SUMMARY OF THE INVENTION

This invention embodies a new apparatus which enables the measurement of the electroplating solution's throwing power under well-controlled hydrodynamic conditions. With this equipment the throwing power of commercially available solutions was measured in a comparison to the HB method for low-speed solutions and also for high-speed solutions.

The invention embodies an instrument for and a method of measuring the throwing power of electrolytes. The instrument is in a form of an elongated cylindrical body adapted for rotation about its longitudinal axis and includes a fixed conductive anode element and at least two cathode elements, at least one of which is variably spaced from the anode element. Preferably, one cathode element is fixed relative to the anode element a first predetermined distance and another cathode element is spaced from the anode element a second variable distance which is a multiple of the first distance. The instrument also includes means for providing current to the anode element and equi-potentially to each of the cathode elements. The measuring includes providing each of the cathode elements with a pre-weighed removable metal foil, rotating the instrument while the anode and cathode elements are completely submerged in an electrolyte, applying current to the anode and the cathode elements, removing the metal foils from the cathode elements and weighing the metal foils with the deposit thereon to compare the weight of deposited metal at different cathode element positions.

DETAILED DESCRIPTION

Figure 1:
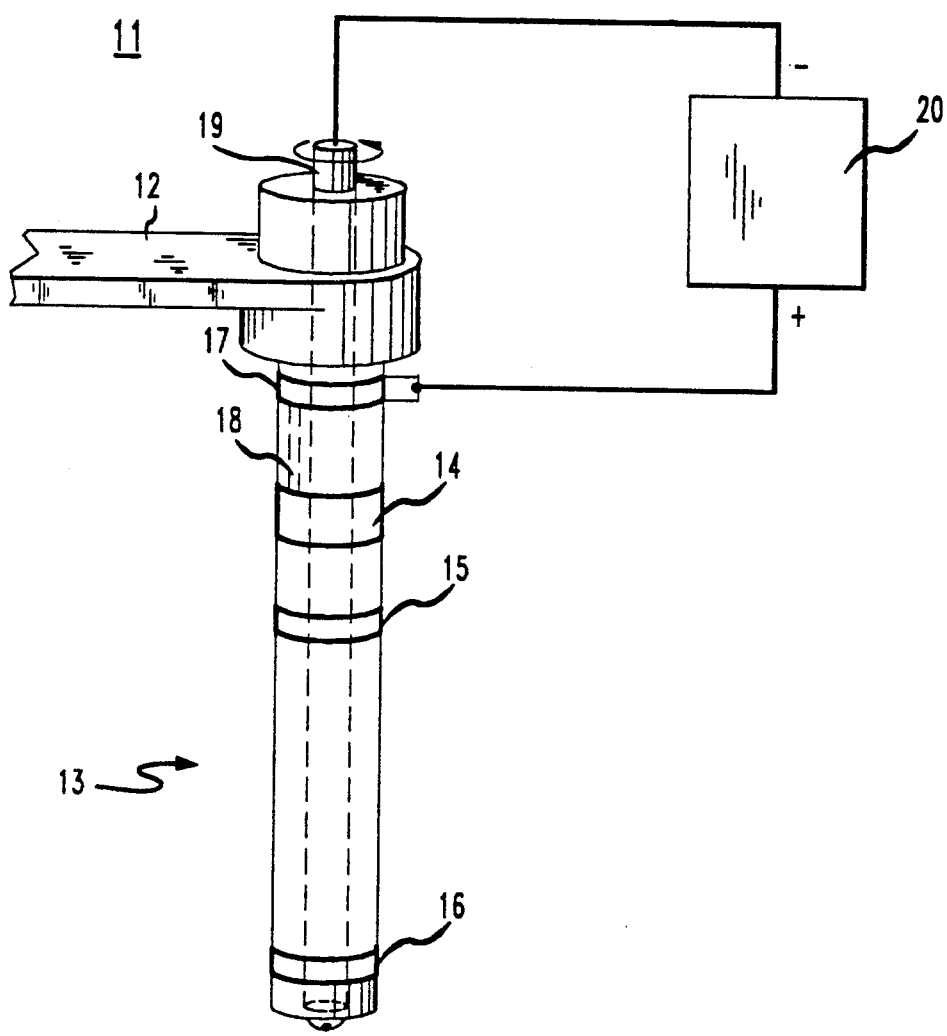
FIG. 1 is a schematic representation of an RCTPE.

In FIG. 1 is shown a throwing power measuring unit, hereinafter referred to as a Rotating Cylinder Throwing Power Electrode (RCTPE), which allows measurements of the throwing power parameter under well-defined hydrodynamic conditions within a wide range of solution agitation.

The (RCTPE) includes an elongated cylindrically-shaped measuring instrument, 11, adapted for rotation about its longitudinal central axis. Instrument 11 is suspendable in an electrolyte (not shown) which may be in its own container or in a plating tank. An arm, 12, supports instrument 11 for suspension in the electrolyte and includes a suitable drive means, such as a belt drive or a motor (not shown), enabling rotation of instrument 11 about its longitudinal axis. Drive means is for providing rotation to instrument 11 about its longitudinal axis at a desired rate of rotation. The rate of rotation may be selected within a range of from 10 to 10,000 RPM, which translates into solution velocity movement past the anode and cathode elements in the range of from 1 to 1,000 cm/sec.

Instrument 11 includes an elongated cylinder, 13, of a suitable electrically non-conducting material, an anode element, 14, arranged coaxially with the cylinder at an upper part thereof and a pair of cathode elements, 15 and 16, arranged coaxially with the cylinder in a descending order along the length of cylinder 13 below the anode element. A slip ring electrode contact, 17, placed above and spaced from the anode element is provided on the cylinder for providing current to the anode element via an insulated lead, 18. Current to the cathode elements may be provided in a similar manner or, alternatively, via a centrally located metal drive shaft, 19, which is being used for rotating the cylinder. Contact 17 is electrically connected to a positive (anode) side of an energy source, 20. The negative (cathode) side of the energy source is connected to an electrical contact for the cathode element, such as drive shaft 19. The shaft may be secured to the insulating cylinder by suitable means such as screws or an internally threaded end cap.

Upper cathode element 15 which is close to the anode element is fixed at a predetermined distance from the anode element, while lower cathode element 16 can be placed at several coaxial positions relative to the anode and the upper cathode, such as at four exemplary positions which give 5/1, 4/1, 3/1 and 2/1 distance ratios of the lower and the upper cathode elements relative to the anode position, respectively. The first number of each ratio denotes the distance from the anode element to the lower cathode element position and the second number of the ratio denotes the distance from the anode element to the upper cathode element position.

The two cathode elements are positioned on the same side of the anode element. This is contrary to the positioning of the anode element between the two cathode elements, as occurs in the Haring Blum cell. In the latter arrangement, the cathode elements have minimal interference with each other's electric fields. In the present arrangement the cathode element nearest to the anode element tends to reduce the current flow to the farther cathode element. While in the Haring Blum cell the arrangement favors a better current distribution, the present arrangement was selected because of its practical application. This condition is more realistic than the Haring Blum arrangement, because in reality plated parts are monolithic, facing the anode from one side.

Cylinder 13, or at least electrically non-conducting parts thereof, is made of an electrically non-conducting material which is not adversely affected by the plating reaction and is non-contaminating with respect to the solution. Suitable material for the cylinder may be selected from such insulating materials as epoxy, polyethylene, polypropylene, polyvinyl chloride, Teflon, glass and other materials possessing the above qualities. Anode element 14 and cathode elements 15 and 16 are made of a metal which also is non-reacting with plating solutions and is non-contaminating with respect to the plating solution. Stainless steels and such refractory metals as titanium, niobium and tantalum are metals suitable for this purpose. Drive shaft 19 may be made of a similar metal.

An operator may use a plurality of instruments 11, each having lower cathode element 16 at a different distance from anode element 14. This would permit the use of a variety of instruments 11 for a corresponding variety of distance ratios.

Figure 2:
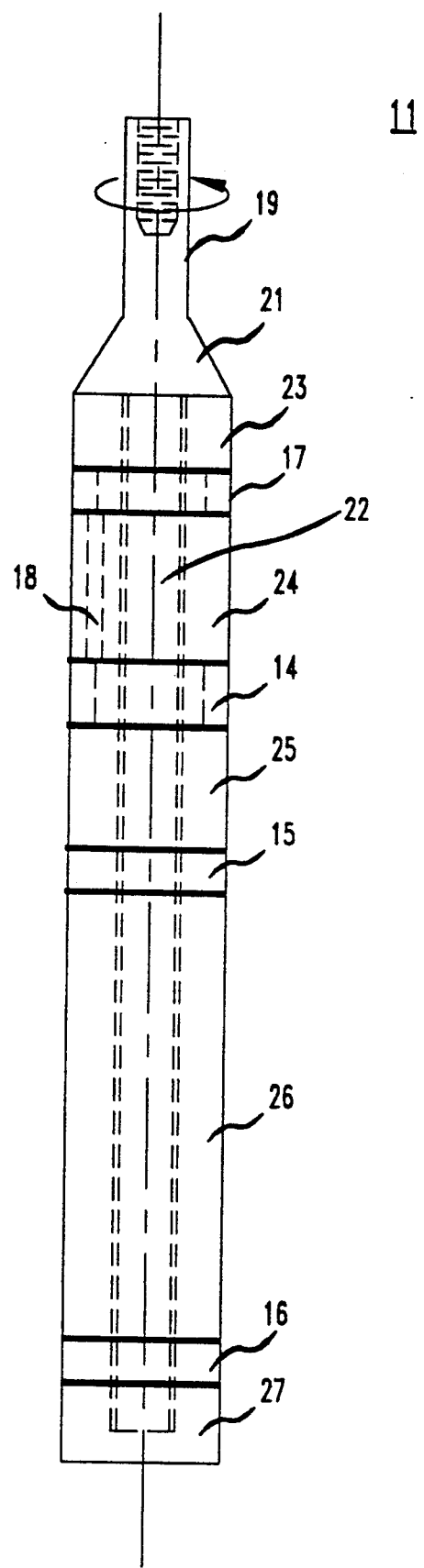
FIG. 2 is a schematic representation of a preferred embodiment of the RCTPE with lower and upper cathode elements at a 5/1 distance ratio from the anode element.

In a preferred embodiment of the invention shown in FIG. 2, instrument 11 is a composite of a drive shaft 19 with a plurality of insulator and conductive portions. This is used for the purpose of having only one set of the drive shaft, the anode element and cathode elements which, when used with a set of separate insulating annular spacers, permit the use of the instrument for a variety of distance ratios. In this embodiment, the drive shaft 19 is provided with a shoulder portion 21 and a central shaft portion 22 of a smaller diameter than the shoulder portion. The remainder of the cylinder is made up of annular non-conducting sections, 23, 24, 25, 26, and a non-conducting capping end section, 27.

Figure 2A:
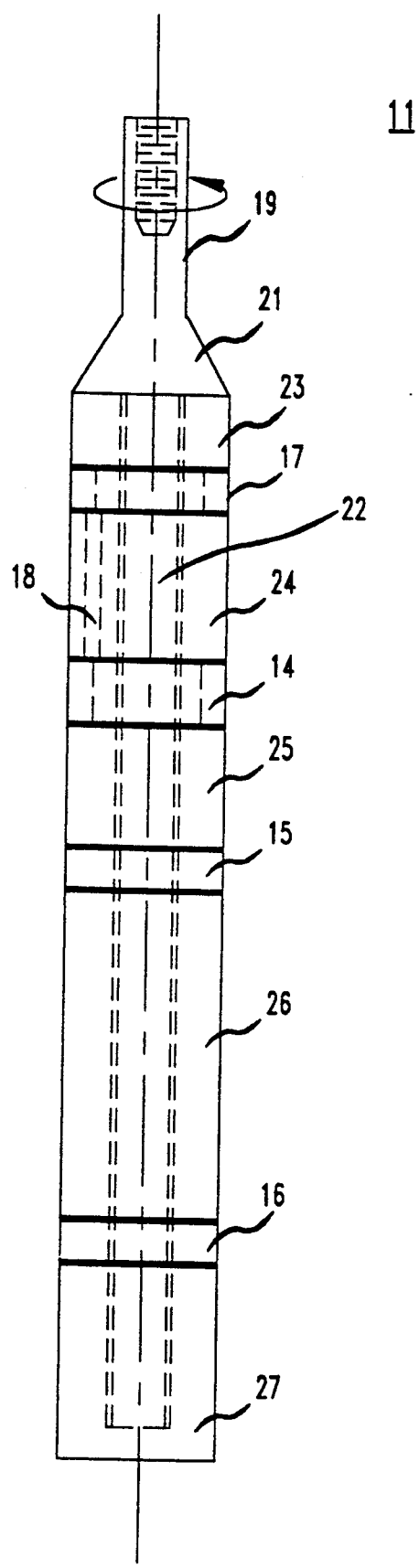
FIG. 2A is a schematic representation of the preferred embodiment of the RCTPE with lower and upper cathode elements at a 4/1 distance ratio from the anode element.
Figure 2B:
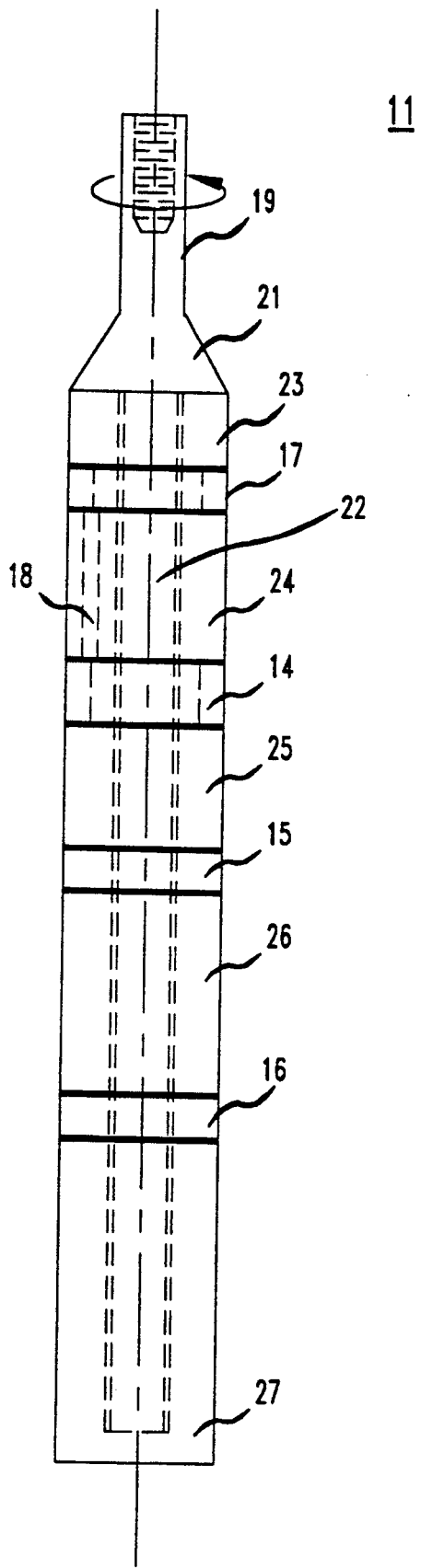
FIG. 2B is a schematic representation of a preferred embodiment of the RCTPE with lower and upper cathode elements at a 3/1 distance ratio from the anode element.
Figure 2C:
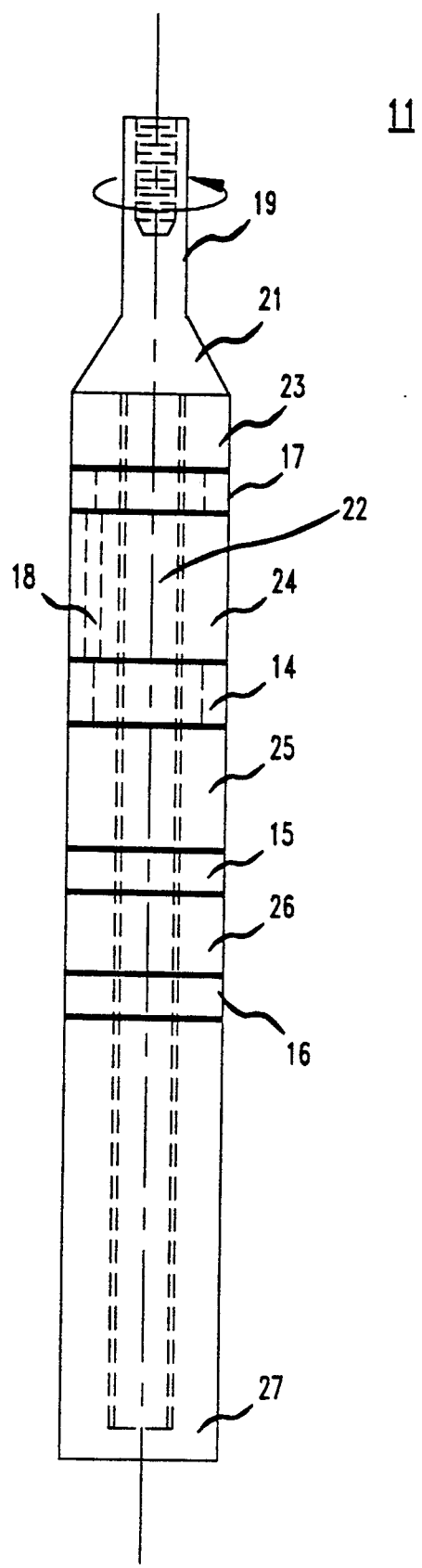
FIG. 2C is a schematic representation of the preferred embodiment of the RCTPE with lower and upper cathode elements at a 2/1 distance ratio from the anode element.

Contact 17 and anode element 14 are spaced from metallic central shaft 22, while cathode elements 15 and 16 are in tight electrical contact with shaft 22. Each of sections 23 and 24 has a portion with a reduced diameter so that the contact and the anode element are insulated from shaft 22. The length of cylinder section 23 is such as to avoid shorting between the shoulder portion 21 and the contact. The length of cylinder section 24 is sufficient to permit immersion of anode element 14 in an electrolyte and yet to avoid wetting of the contact sleeve by the electrolyte. Section 25 is of a length enabling spacing between the anode element and upper cathode element 15 a first predetermined distance. Section 26 is of a length, which together with section 24 and cathode element 15 adds to a spacing between the anode element and lower cathode element 16 a second predetermined distance equal to a multiple of said first predetermined distances. For example, in the embodiment shown in FIG. 2, the spacing between anode element 14 and cathode element 15 is equal to a certain unitary length, while the spacing between anode element 14 and cathode element 16 is equal to five times the unitary length. This results in a distance ratio of 5:1 (anode element to lower cathode element 16 and anode element to upper cathode element 15). In those instances when it is desirable to test throwing power at other distance ratios, sections 26 and 27 may be replaced by at least two other sections permitting positioning of the lower cathode element at 4:1, 3:1 and 2:1 distance ratio positions as is schematically represented in FIGS. 2A, 2B and 2C, respectively. In some instances, more than two lower cathode elements may be used on the instrument. For example, upper cathode element 15 and two lower cathode elements may be positioned at 1, and at 3 and 5 distance positions relative to the anode element.

Cathode elements 15 and 16 may be secured on central shaft 22 by a tight fit, a key hole, by means of screws and in other known manner. It is important that an efficient electrical contact exists between these cathode elements and the central shaft. In the preferred embodiment, at least the lower portion of the central shaft and the cathode elements are provided with matching threads. This ensures the electrical contact and permits the use of a non-conducting end cap 27 securable to the end of the central shaft by means of matching threads. The cap forces individual portions of the cylinder in contact with shoulder 21 of drive shaft 19.

The measurement of the throwing power is performed by attaching pre-weighed copper foils on two cathode elements and conducting the deposition under well-defined conditions of cylinder rotation, that is, under identical mass transport conditions. This is particularly important for the high-speed bath tests (e.g. 200 RPM and higher) and is helpful in low-speed bath tests (e.g. up to 200 RPM) where readings can be masked by hydrogen evolution which can interfere with rotation generated transport conditions.

Two groups of tests have been performed. One group of tests consists of low-speed measurements. These were used to make a comparison between the information that was obtained from the Haring-Blum cell and the RCTPE, such as the effects of solution agitation and the cathode distance ratio on the throwing power. The high-speed tests were used to measure the throwing power of the high-speed solutions and correlate the data to practical experience. The reproducibility of the operation is excellent as shown in the following data.

| Parameters: | Low-Speed Test Matrix: | |
|---|---|---|
| | Haring Blum Cell | RCTPE |
| Current Density | 5 ASF | 5 ASF |
| Solution Agitation | 25 cm/s (250 RPM) | 5,10,25, cm/s |
| Distance Ratio | 5/1 & 3/1 | 5/1, 4/1, 3/1 & 2/1 |
| Temperature | 35–40° C. | 35–40° C. |

| Solutions Tested & Their Formulations: | | |
|---|---|---|
| 1. Gold Plating Solutions: | | |
| Component | Soft Gold | Hard Gold |
| Au | 8 g/l | 8 g/l |

-continued

|  | | |
|---|---|---|
| Co | — | 100 ppm |
| Conducting Salt | 130 g/l | 130 g/l |
| monobasic potassium phosphate | 4 g/l | — |
| Brightener salt | 30 g/l | 30 g/l |

2. Palladium Plating Solutions:

| Component | Pd Acid Strike | Pd Plate | Pd Thick & Ductile | PdNi NFS |
|---|---|---|---|---|
| Pd | 3 g/l | 5 g/l | 5 g/l | 5 g/l |
| NaCl | 60 g/l | — | — | — |
| Ni | — | — | — | 2.5 g/l |
| Dipotassium hydrogen phosphate | — | 90 g/l | 90 g/l | — |
| Ammonium Chloride | — | — | 80 g/l | 80 g/l |
| Ligand (proprietary) | — | 25 ml/l | — | — |
| Additive II proprietary brightener | — | — | 4 ml/l | — |
| Additive IVS proprietary brightener | — | — | — | 2 ml/l |
| Potassium hydroxide | — | to pH 11.0 | to pH 8.0 | to pH 7.7 |
| HCl (33%) | to pH 3.9 | — | to pH 8.0 | to pH 7.7 |

3. Rochelle Copper Low Speed:

| Component | Amount |
|---|---|
| Rochelle Salt | 15 g/l |
| CuCN | 30 g/l |
| KCN | 50 g/l |
| KOH | 5 g/l |
| $K_2CO_3$ | 15 g/l |

| Parameters | High-Speed Test Matrix RCTPE |
|---|---|
| Current Density | 100 ASF (Unless otherwise specified) |
| Solution Agitation | 25, 50, 100, 200 cm/s |
| Distance Ratio | 5/1, 4/1, 3/1 & 2/1 |
| Temperature | 35–40° C. (Except NI sulfamate, which was plated at 60° C.) |

Solutions:

1. Soft Gold Plating Solution:

| Component | Soft Gold |
|---|---|
| Au | 25 g/l |
| Conducting Salt | 130 g/l |
| monobasic potassium phosphate | 4 g/l |
| Brightener salt | 30 g/l |

2. Palladium Plating Solutions:

| Component | Pd Acid Strike | Pd Plate | PdNi NFS | Pd Thick & Ductile | Pd NFS |
|---|---|---|---|---|---|
| Pd | 10 g/l | 25 g/l | 25 g/l | 25 g/l | |
| NaCl | 60 g/l | — | — | — | — |
| Ni | — | — | — | 15 g/l | — |
| Dipotassium hydrogen phosphate | — | 90 g/l | 90 g/l | — | — |
| Ammonium Chloride | — | — | 80 g/l | 80 g/l | 80 g/l |
| Ligand (proprietary) | — | 50 ml/l | — | — | — |
| Additive II proprietary brightener | — | — | 4 ml/l | — | — |
| Additive IVS proprietary brightener | — | — | — | 2 ml/l | — |
| Additive VS proprietary brightener | — | — | — | — | 2 ml/l |
| Potassium hydroxide | — | to pH 11.0 | to pH 8.0 | to pH 7.7 | to pH 7.7 |
| HCl (33%) | to pH 3.9 | — | to pH 8.0 | to pH 7.7 | to pH 7.7 |

3. Rochelle Copper High Speed:

| Component | Amount |
|---|---|
| Rochelle Salt | 60 g/l |
| CuCN | 42 g/l |
| KCN | 67 g/l |
| KOH | 10 g/l |
| $K_2CO_3$ | 30 g/l |

4. Ni Sulfamate High Speed Solution:

| Component | Amount |
|---|---|
| Ni sulfamate | 600 g/l |
| Ni Chloride | 10 g/l |

| -continued | |
|---|---|
| Boric Acid | 45 g/l |

The measured data is presented in an empirical form with the actual ratios of the weights obtained. Equation (1) defines the throwing power, TP, measure used in presenting the data.

$$TP = WN/WF \qquad (1)$$

where WN is the weight of deposit at the near cathode and WF weight of deposit at the far cathode. In each case, the number is a relative measure, in percent, of the closeness to an ideal case of having a ratio of weights close to a unity. Thus, baths with a good throwing power have ratios close to the unity, and baths with inefficient throwing power have numbers which differ from unity.

Figure 3:
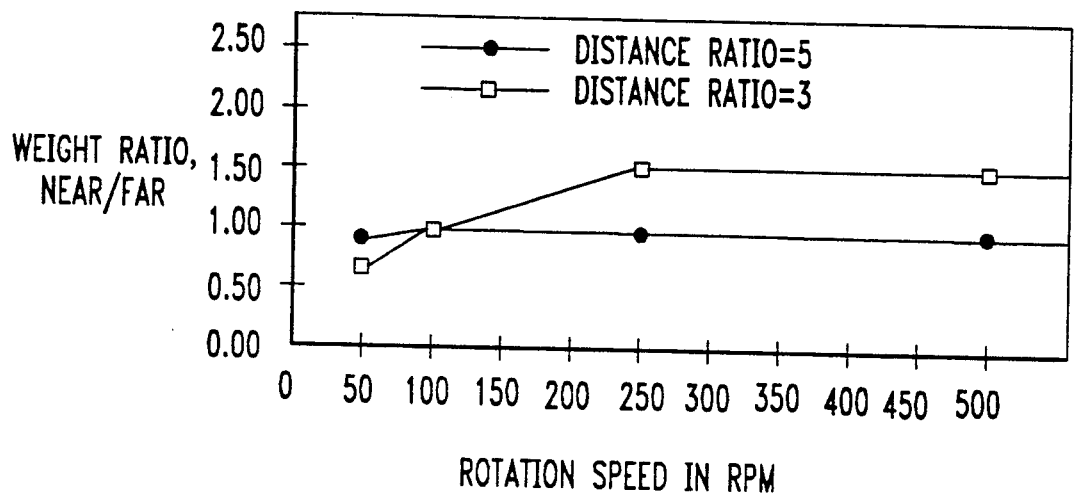
FIG. 3 is a plot of an effect of rotation speed on the throwing power of Rochelle copper low-speed plating solutions, as measured with the lower and upper cathode elements at distance ratios of 5/1 and 3/1 from the anode element, and at 50 to 500 RPM (5–50 cm/s)
Figure 4:
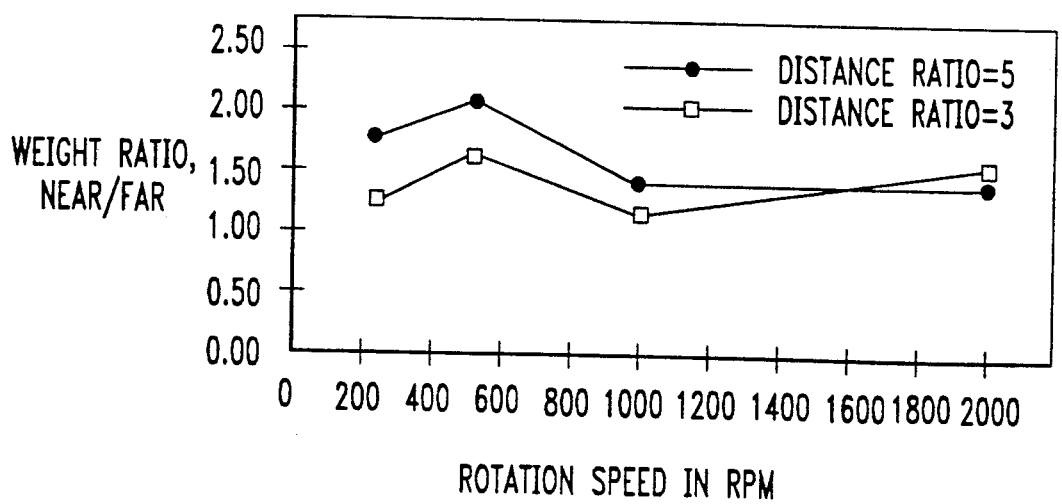
FIG. 4 is a plot of an effect of rotation speed on the throwing power of Rochelle copper high-speed plating solutions as measured with the lower and upper cathode elements at distance ratios of from 5/1 and 3/1 from the anode element and at 200 to 2,000 RPM (20–200 cm/s)

Since the transport of matter is apparently the key parameter in conducting these measurements, the magnitude of this effect was established first. The RCTPE system offers an opportunity to investigate the throwing power dependence on solution agitation under well-defined conditions. This effect was measured on the Rochelle copper bath for both low and high-speed conditions. The comparison was made for two distance ratios, 5/1 and 3/1 (FIGS. 3 and 4). The low-speed measurements are presented in FIG. 3. At low agitation rates of 50 and 100 RPM (5 cm/sec and 10 cm/sec) the throwing power is good (weight ratio is close to 1). With increased solution agitation the measurements diverge. At 500 RPM (50 cm/sec) the weight ratio at 5/1 distance ratio is approximately ½ of the weight ratio at the 3/1 distance. The effect is possibly due to an overall lower current efficiency of the process. At the 5/1 distance ratio the metal deposition process is clearly less efficient (only ½ the metal deposited) than at the 3/1 distance ratio. This indicates an excessive hydrogen evolution at 5/1 ratio. Data presented in FIG. 3 suggest that the low-speed processes should be investigated at lower solution agitation, possibly 250 RPM (25 cm/sec) or less, e.g. at 100 RPM (10 cm/sec).

The high-speed measurements are presented in FIG. 4. Convergence is quite good, for the 5/1 and the 3/1 distance ratio. This is especially true for the 1000 (100 cm/sec) and 2000 RPM (200 cm/sec) rates. Here the weight ratio is close to unity, which matches the empirically established good performance of the Rochelle copper solution. Therefore, the 1000 RPM (100 cm/s) is adopted as the nominal solution velocity in the RCTPE measurements of the throwing power for high speed solutions.

Figure 5:
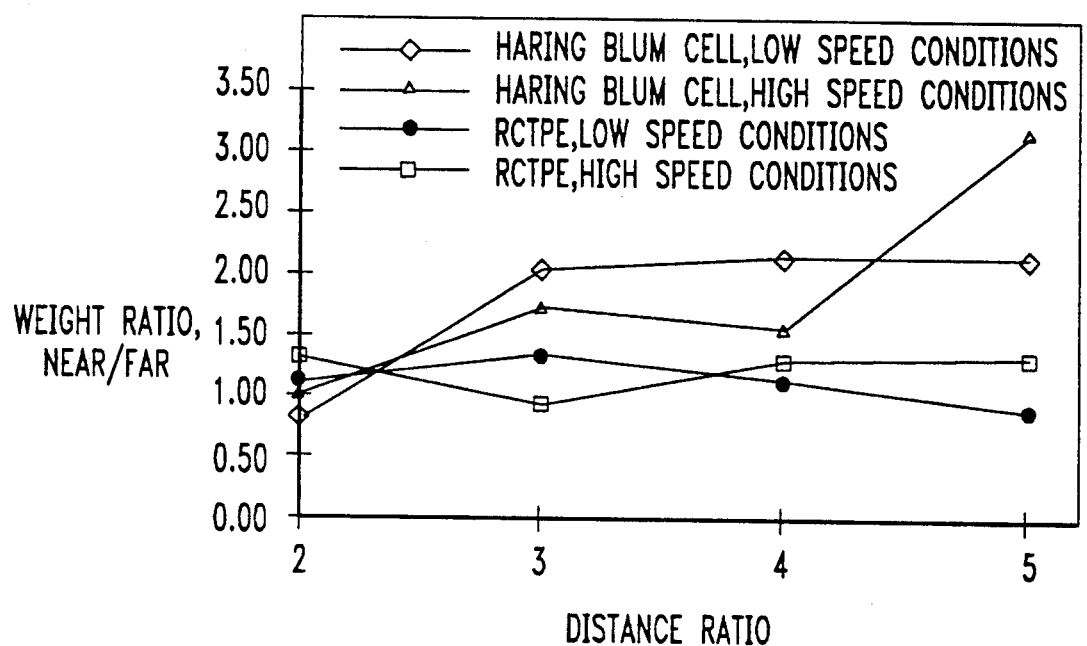
FIG. 5 is a plot of an effect of distance ratios on the throwing power for Rochelle copper plating solutions, comparing measurement with RCTPE at low and high-speed conditions with those of Haring Blum cell.

FIG. 5 shows the throwing power data as a function of the distance ratio, from 2/1 to 5/1 for low-speed Rochelle copper as measured using both the Haring Blum cell and the RCTPE. Although the distance ratio was changed considerably, the observed values stayed within narrow limits for the RCTPE. The Haring Blum data varied over a much wider range for the same distance ratios, suggesting that the RCTPE method is more internally consistent, which is required for plating process characterization.

Figure 6:
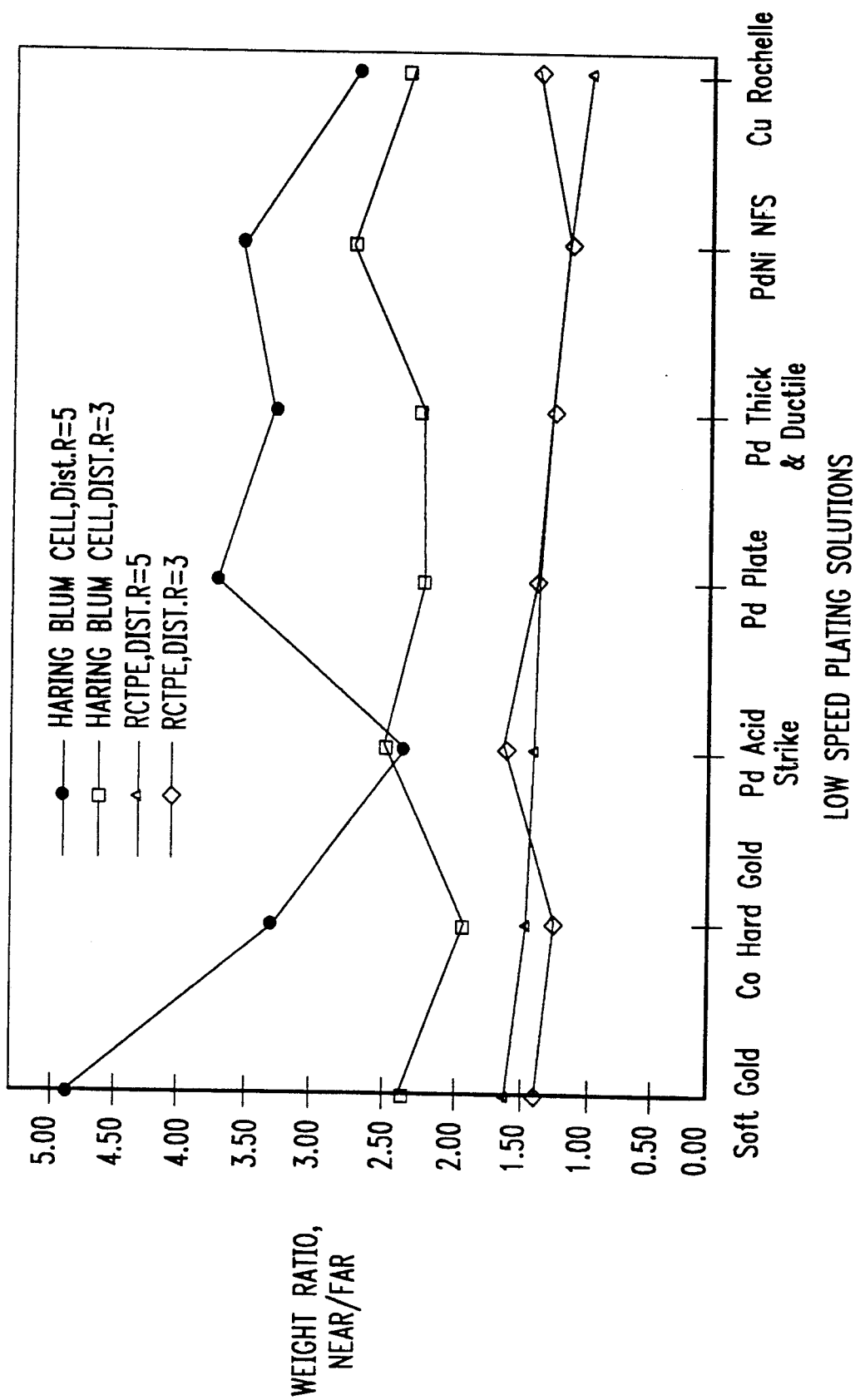
FIG. 6 is a plot of comparison of RCTPE and Haring Blum cell throwing power data for selected low-speed plating solutions at distance ratios of 5/1 and 3/1.

Reference information on a variety of low-speed plating solutions was established for comparison of the Haring-Blum cell and RCTPE at distance ratios of 5/1 and 3/1. FIG. 6 shows data presented in the descending order of weight ratio for the 5/1 distance ratio. Superior performance was demonstrated by Pd Thick Ductile, PdNi NFS (non-foaming) and, as expected, Rochelle Copper. The RCTPE data was highly convergent, while the Haring Blum data was quite divergent and spanned a wider range of values. In addition, the range of values of the RCTPE data is supported by practical experience with the tested plating solutions.

Figure 7:
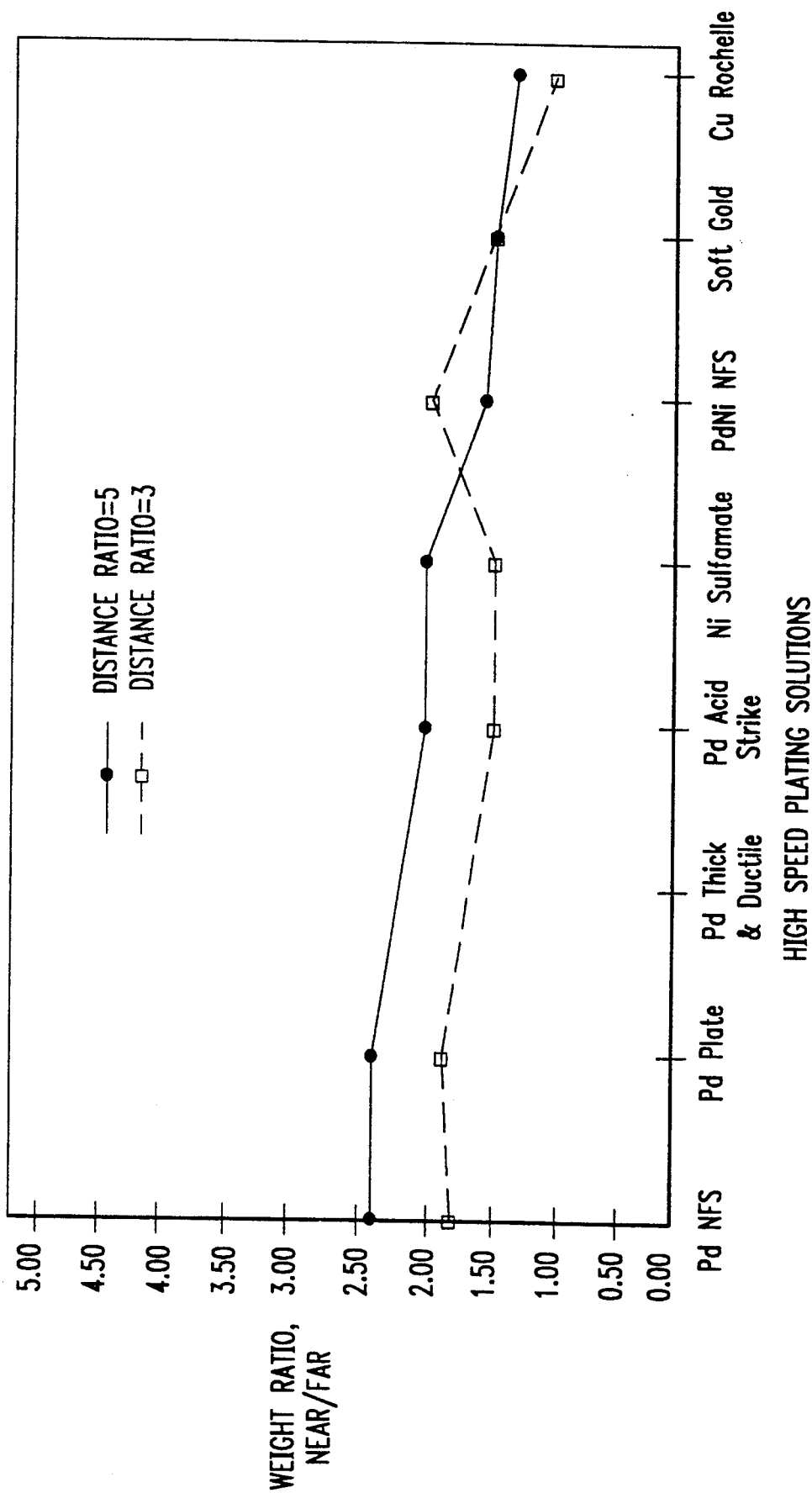
FIG. 7 is a plot of throwing power of RCTPE for select high-speed plating solutions, at distance ratios of 5/1 and 3/1.
Figure 8:
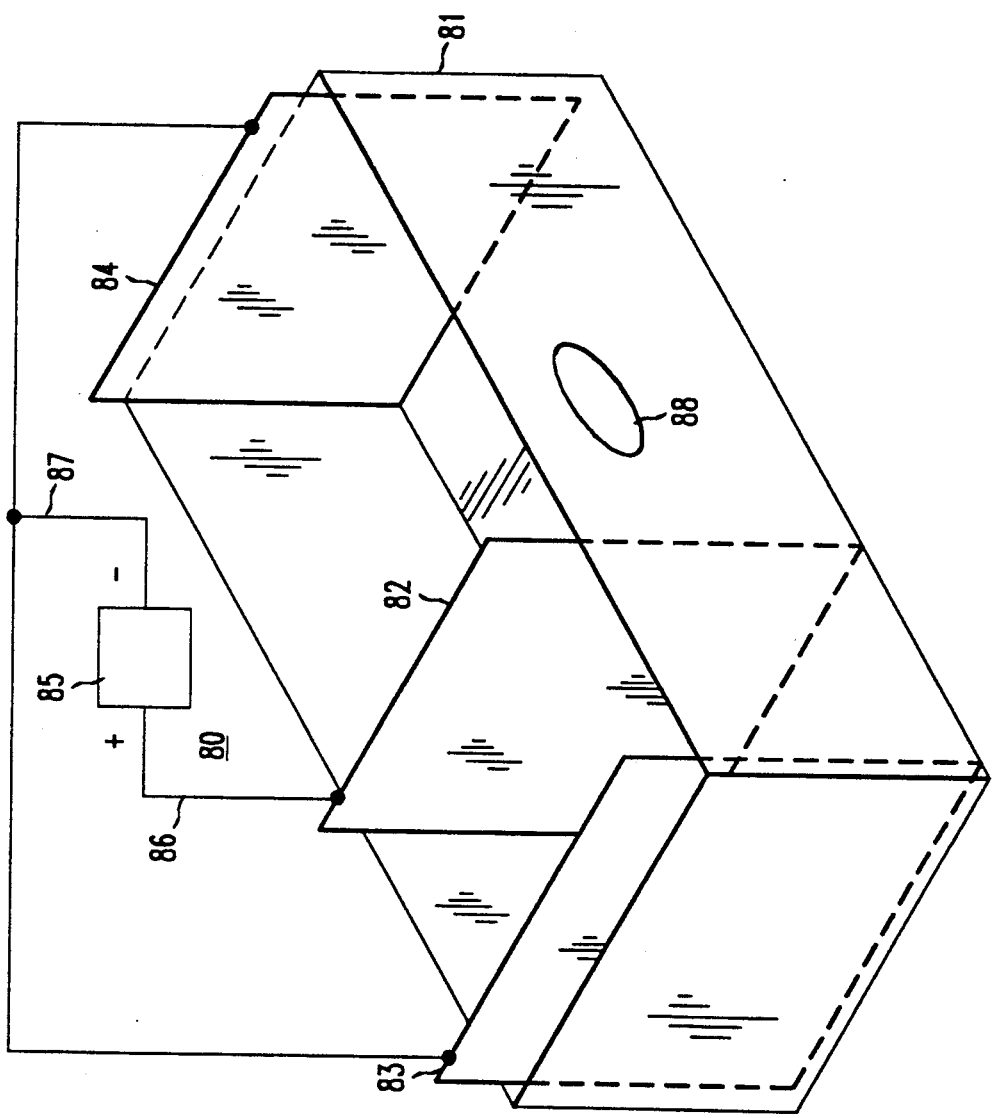
FIG. 8 is a schematic representation of a Haring-Blum cell.

FIG. 7 shows the performance of a variety of high-speed solutions measured with the RCTPE at 1000 RPM (100 cm/s). Rochelle Copper again showed superior performance. Soft gold and palladium nickel alloy were also quite good. The graph also shows a clear convergence of the data, as did the low-speed data presented in FIG. 6.

A throwing power rating system, which is presented in the Table below, was prepared to evaluate the RCTPE as a potentially useful tool for measuring functional performance of plating solutions. The TP data were divided into categories from excellent to poor. As a reference, the same terminology was used as in *ASTM 02.05 Designation: B*-507 "Standard Practice for Design of Articles to be Electroplated on Racks", which defines the throwing power capability of plating solutions.

| Weight Ratio, Near/Far | Throwing Power Rating |
|---|---|
| 0.75–1.25 | Excellent |
| 1.25–2.0/0.75–.5 | Good |
| 2.0–2.5/0.5–0.25 | Fair |
| >2.5/<.25 | Poor |

In the table below are presented the results of a comparison of various plating solutions using the above arbitrary scale. It is clear that the RCTPE gave internally consistent results which are also in better agreement with the ASTM guidelines.

| Bath | ASTM Rating | Haring Blum | Haring Blum | RCTPE | RCTPE |
|---|---|---|---|---|---|
| Distance Ratio | — | 5:1 | 3:1 | +5:1 | 3:1 |
| Rochelle Cu, LS | Excellent | Fair | Fair | Excellent | Excellent |
| Rochelle Cu, HS | Excellent | Poor | Fair | Excellent | Excellent |
| Soft Gold, LS | Good | Poor | Fair | Good | Good |
| Soft Gold, HS | Good | — | — | Good | Good |
| Ni Sulfamate, LS | Fair | Poor | Good | — | Fair |
| Ni Sulfamate, HS | Fair | — | — | Fair | Good |

Additional advantages and modifications will readily occur to those skilled in the art. Therefore, the invention in its broader aspects is not limited to the specific details, representative devices, and illustrated examples shown and described. Accordingly, various modifications may be made without departing from the spirit or scope of the general inventive concept as defined by the appended claims and their equivalents.

We claim:

1. An instrument for measuring throwing power of an electrolyte, which comprises:

an elongated cylindrical body adapted for rotation about the longitudinal axis thereof, said cylindrical body having substantially uniform diameter and comprising a plurality of metallic annular elements which are arranged along the longitudinal axis of the body and which are separated from each other by non-conducting, annular elements, one of said metallic annular elements is a short metallic anode element positioned coaxially of the cylindrical body toward an upper end thereof, and at least two of said metallic annular elements are short metallic cathode elements positioned coaxially of and along the length of said body in spaced relation each to another and to said anode element, said cathode elements being on the same side of the cylindrical body relative to the anode element, one of said cathode elements being at a fixed distance from the anode element, and the other of said cathode elements being at a second selectively variable distance from the anode, said second distance being greater than the fixed distance and being a whole number multiple of said fixed distance, and means for providing current to the anode element and equi-potentially to said cathode elements such that, upon immersion of said instrument in an electrolyte with said anode element and the cathode elements submerged in the electrolyte, and application of plating potential to the anode and the cathodes, an electro-deposition takes place on the cathode elements.

2. The instrument of claim 1 in which said second distance is selected from a range of from 2 to 5 multiples of the fixed distance from the anode element.

3. The instrument of claim 1 in which said cylindrical body comprises a drive shaft passing through said plurality of metallic annular elements and non-conducting annular elements, beginning with a non-conducting annular element and ending with a non-conducting annular capping element.

4. The instrument of claim 1 in which one of said means for providing current to the cathode elements is an extension of a drive shaft, passing through said plurality of the annular elements and being in electrically conductive contact with the said cathode elements.

5. The instrument of claim 1 in which each of said cathode elements further comprises a metal foil removably secured to an outer surface of the cathode element.

* * * * *